(12) United States Patent
Halamish (10) Patent No.: US 6,877,509 B2
(45) Date of Patent: Apr. 12, 2005

(54) AEROSOL INHALATION INTERFACE

(75) Inventor: Asaf Halamish, Karkur (IL)

(73) Assignee: Baby's Breath Ltd., D.N. Hefer (IL)

( * ) Notice: Subject to any disclaimer, the term of this patent is extended or adjusted under 35 U.S.C. 154(b) by 87 days.

(21) Appl. No.: 10/297,829

(22) PCT Filed: Jun. 29, 2001

(86) PCT No.: PCT/IL01/00601

§ 371 (c)(1),
(2), (4) Date: Dec. 11, 2002

(87) PCT Pub. No.: WO02/02052

PCT Pub. Date: Jan. 10, 2002

(65) Prior Publication Data

US 2004/0031484 A1 Feb. 19, 2004

(30) Foreign Application Priority Data

Jul. 5, 2000 (IL) .................................... 137185

(51) Int. Cl.⁷ .......................................... A61M 11/00
(52) U.S. Cl. .............................. 128/200.14; 128/200.18
(58) Field of Search ................... 128/200.14, 201.29, 128/202.12, 202.19, 204.15, 205.26, 200.18

(56) References Cited

U.S. PATENT DOCUMENTS

| | | | |
|---|---|---|---|
| 50,641 A | * 10/1865 | Stone et al. ............... 454/238 |
| 113,536 A | * 4/1871 | Leland et al. ........... 128/202.12 |
| 222,888 A | * 12/1879 | Garland ....................... 239/418 |
| 314,453 A | * 3/1885 | Ketchum ................ 128/202.12 |
| 365,067 A | * 6/1887 | Harris .................... 128/202.12 |
| 491,430 A | * 2/1893 | Longstreth et al. .... 128/200.14 |
| 912,742 A | * 2/1909 | Shute ..................... 128/202.26 |
| 1,669,683 A | * 5/1928 | Temple et al. .............. 126/205 |
| 1,971,408 A | * 8/1934 | Heldbrink et al. ..... 128/205.26 |
| 2,627,217 A | * 2/1953 | Hainke et al. ............... 454/66 |
| 3,050,058 A | * 8/1962 | Andrews, Jr. .......... 128/204.16 |
| 3,232,292 A | * 2/1966 | Schaefer ................ 128/200.14 |
| 3,385,036 A | * 5/1968 | Webb ........................... 55/418 |
| 3,565,072 A | * 2/1971 | Gauthier ................ 128/200.16 |
| 3,902,488 A | * 9/1975 | Sheppard ............... 128/200.14 |
| 3,949,743 A | * 4/1976 | Shanbrom .............. 128/200.14 |
| 4,577,628 A | * 3/1986 | Hickmann ............. 128/205.26 |
| 4,593,688 A | 6/1986 | Payton ................... 128/200.28 |
| 4,677,975 A | * 7/1987 | Edgar et al. ........... 128/200.14 |
| 4,819,629 A | * 4/1989 | Jonson ................... 128/203.22 |
| 4,984,158 A | * 1/1991 | Hillsman ............... 128/200.14 |
| 5,063,922 A | * 11/1991 | Hakkinen .............. 128/200.16 |
| 5,167,506 A | * 12/1992 | Kilis et al. ................... 434/262 |
| 5,233,975 A | * 8/1993 | Choate .................. 128/200.14 |
| 5,253,641 A | * 10/1993 | Choate .................. 128/200.14 |
| 5,320,094 A | * 6/1994 | Laube et al. ........... 128/203.12 |
| 5,363,842 A | * 11/1994 | Mishelevich et al. .. 128/200.14 |
| 5,372,126 A | * 12/1994 | Blau ...................... 128/200.14 |
| 5,404,871 A | * 4/1995 | Goodman et al. ..... 128/200.14 |
| 5,803,063 A | 9/1998 | Corey ................... 128/203.12 |
| 5,853,002 A | 12/1998 | Kawasaki .............. 128/200.14 |

* cited by examiner

Primary Examiner—Aaron J. Lewis
(74) Attorney, Agent, or Firm—Welsh & Flaxman LLC (57) ABSTRACT

The present invention is an aerosol inhalation interface, and a method for its use. The device delivers a flow of aerosol medication to a patient breathing tidally by creating a medication rich environment proximal to the nose and mouth of the patient, while the patient is in a reclining position. The device, which is suspended above the patient's nose and mouth, is comprised of an aerosol generator, which generates medicated particles; a containment region, into which the generator discharges the medicated particles; a downwardly projecting outlet sleeve, which is connected to the containment region and channels the particles from the containment region to create a medication rich environment proximal to the nose and mouth of the patient; and an air movement deflector, which inhibits the dispersion of the particles and disturbance of the medication rich environment.

23 Claims, 8 Drawing Sheets

AEROSOL INHALATION INTERFACE

FIELD AND BACKGROUND OF THE INVENTION

The present invention relates to an aerosol inhalation interface and, in particular, it concerns a method and a device for the delivery of a flow of aerosol medication to a tidally breathing patient, while the patient is in a reclining position, with the device suspended above the patient's nose and mouth. The present invention further concerns a method for determining the effectiveness of inhalation therapy, while the therapy is in progress.

It is known that some inhalation therapy devices and methods require special breathing techniques, such as breathing in synchronization with a device or taking hard deep breaths. These techniques are impossible for some patients such as infants and very young children, patients with limited mental capacity, patients who are very weak, or patients with limited lung capacity.

It is further known that it is difficult to administer aerosol medications to infants and small children due to their shortened capacity to tolerate treatment.

It is further known that it is difficult to monitor or evaluate therapeutic effectiveness of treatments administered to infants and small children because they are unable to answer treatment related questions reliably or not at all.

There are further known devices that disguise a medication interface in a toy, such as a telephone (U.S. Pat. No. 5,803,063) or a puppet (U.S. Pat. No. 5,853,002). These devices are designed to attract the child's attention to the device, but do not increase their effectiveness.

There are further known devices for inhalation therapy that are attached directly to the child, such as masks and the apparatus claimed in U.S. Pat. No. 4,593,688. These devices may increase the effectiveness of medication delivery, however, they are cumbersome and may even be scary for infants and small children. This may affect the child's breathing during treatment and greatly decrease the effectiveness of the therapy.

There are further known devices that encapsulate the entire child, such as tents, or just their head, such as hoods, so as to control the entire breathing environment. These devices require the environment to be sealed, which may take some minutes to accomplish and can use up some of the child's tolerance for treatment. These devices also require that they remain sealed throughout the treatment session. For some children, this may be difficult, and may interfere with calming parental contact as well as raise suffocation concerns due to CO2 retention in a sealed respiratory environment.

There is therefore a need for an aerosol inhalation interface that achieves effective medication delivery; is not scary, as is the case of devices that are attached directly to, or seal in, the patient; is quick and easy to use; allows for soothing parental contact during treatment; and is able to monitor and evaluate the effectiveness of the aerosol inhalation therapy.

SUMMARY OF THE INVENTION

The present invention is a device, an aerosol inhalation interface, for delivering a flow of aerosol medication to a patient, and a method for determining the effectiveness of inhalation therapy, while the therapy is in progress.

According to the teachings of the present invention there is provided, a device for delivering a flow of aerosol medication to a patient breathing tidally and positioned supinely with the device is suspended above the patient's nose and mouth, the device is comprised of: an aerosol generator, which generates a medicated aerosol; a housing associated with the aerosol generator defining a containment region, into which the generator discharges the aerosol, the housing preventing the immediate dispersal of the particles of the aerosol; a downwardly projecting outlet sleeve interconnected to the bottom of the housing so that the aerosol particles move into and through the sleeve, the sleeve channeling the aerosol particles to a region externally proximal to a bottom opening of the sleeve; and an air movement deflector configured to inhibit the dispersion of the particles once the particles arrive at the external region, by reducing ambient air movement.

According to a further teaching of the present invention, the outlet sleeve is downwardly convergent.

According to a further teaching of the present invention, the outlet sleeve is substantially cylindrical.

According to a further teaching of the present invention, the aerosol generator discharges the aerosol in an upward direction.

According to a further teaching of the present invention, the downward flow of the particles into and through the sleeve is solely by gravitational force.

According to a further teaching of the present invention, the particles are electrically charged by an electrical charging system, which includes at least one electrical charging device.

According to a further teaching of the present invention, the electrical charging system charges the surfaces of the housing that define the containment region and the outlet sleeve.

According to a further teaching of the present invention, the surfaces of the housing, the outlet sleeve and the particles are like charged so as to diminish a possible settling of the particles on the surfaces due to electrostatic repulsion.

According to a further teaching of the present invention, the electrical charging system further includes at least one electrode and the particles are like charged so as to enhance the downward flow of the particles due to electrostatic repulsion.

According to a further teaching of the present invention, the patient is electrically grounded so as to facilitate the downward flow of the particles by way of electrostatic attraction.

According to a further teaching of the present invention, an airflow generator moves air downwardly from the containment region, enhancing the downward flow of particles.

According to a further teaching of the present invention, the aerosol generator discharges the aerosol in a downward direction.

According to a further teaching of the present invention, the deflector is non-sealing allowing for exchange of air.

According to a further teaching of the present invention, a control system regulates the operational elements of the device.

According to a further teaching of the present invention, a tidal breathing monitor that is connected to the control system is deployed to monitor the tidal breathing of the patient.

There is also provided according to a further teaching of the present invention, a method for delivery of a flow of aerosol medication to a patient breathing tidally and positioned supinely, by a device being suspended above the patient's nose and mouth, the method is comprised of generating an aerosol of medicated particles, discharging the aerosol in a containment region, the region being defined by a housing, the housing preventing the immediate dispersal of the particles, channeling the particles, by use of a downwardly converging outlet sleeve, toward a region externally proximal to a bottom opening of the outlet sleeve, so as to create a medication rich environment in the external region, and deploying an element configured so as to inhibit the dispersion of the particles once the particles arrive at the external region by reducing ambient air movement.

According to a further teaching of the present invention, the discharging of the particles is in an upward direction.

According to a further teaching of the present invention, the particles begin to flow downward into and through the sleeve, solely by gravitational force.

According to a further teaching of the present invention, the particles are charged.

According to a further teaching of the present invention, the surfaces of the housing and the sleeve are also charged.

According to a further teaching of the present invention, the surfaces, the sleeve and the particles are like charged, so as to diminish a possible settling of the particles on the surfaces, due to electrostatic repulsion.

According to a further teaching of the present invention, an electrode and the particles are like charged, so as to enhance the downward flow of the particles, due to electrostatic repulsion.

According to a further teaching of the present invention, the patient is electrically grounded by a device, so as to enhance the downward flow of the particles by electrostatic attraction.

According to a further teaching of the present invention, the downward flow of the particles is enhanced by downwardly flowing air movement.

According to a further teaching of the present invention, the aerosol generator discharges the aerosol in a downward direction.

According to a further teaching of the present invention, the operational elements of the device are regulated by a control-system.

According to a further teaching of the present invention, a tidal breathing monitor is connected to the control system.

There is also provided according to a further teaching of the present invention, a method for monitoring and determining the effectiveness of aerosol inhalation therapy, while the therapy is in progress, the method is comprised of, establishing a baseline tidal breathing rate, by use of a tidal breathing monitor, beginning therapy, by use of an inhalation therapy device, monitoring tidal breathing rate throughout the therapy, and determining the effectiveness of the therapy by use of data collected.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is a method and a device, an aerosol inhalation interface, for delivering a flow of aerosol medication to a patient, and a method for determining the effectiveness of inhalation therapy, while the therapy is in progress.

The principles and operation of an aerosol inhalation interface and a method for its use according to the present invention may be better understood with reference to the drawings and the accompanying description.

The patient is to be positioned in a reclining position and engaged in tidal breathing, with the device being suspended above the patient's nose and mouth.

Preferred embodiments of the present invention described herein comprise: an aerosol generator, which may be battery operated or plugged into an energy source, or may use compressed air; a containment region, the top of which preferably is removable to allow access to the aerosol generator; a downwardly projecting outlet sleeve, and a non-sealing air movement deflector. Further options included in the examples herein given include, but are not limited to, a control system for regulation of the operational elements of the device; incorporation of a tidal breathing monitor; and enhancing the downward flow of the aerosol particles by electrically charging the aerosol particles, electrically charging the surfaces of the device, electrically grounding the patient, producing downward air flow, or the downward discharge of the aerosol from the aerosol generator. It should be noted that any or all of the options may be used separately or in any combination.

Figure 1:
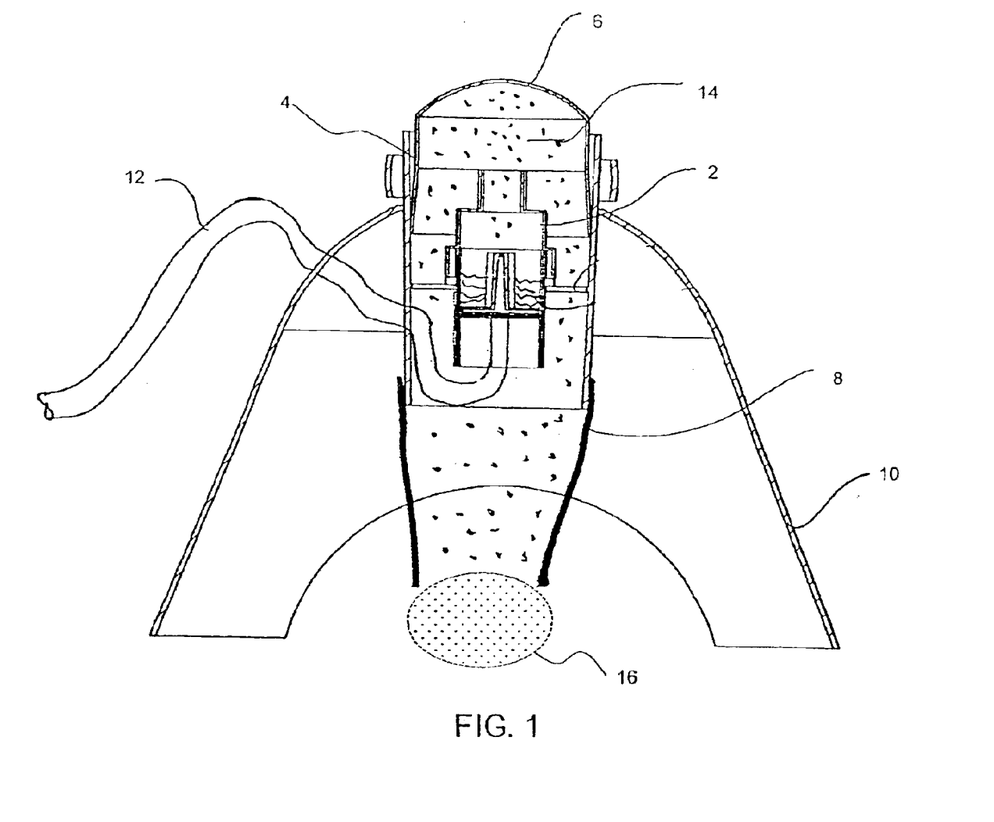
FIG. 1 is a cross-sectional view of a preferred embodiment of the present invention that uses a nebulizer as the aerosol generator.

Referring now to the drawings, FIG. 1 shows a first preferred embodiment of the present invention that utilizes a nebulizer as the aerosol generator 2. The aerosol is a suspension of liquid or solid particles in a gas, in this case air. As pressurized air leaves the end of the air supply hose 12, aerosol particles are discharged into the containment region 14 in an upward direction. The containment region 4 is defined as that region inside of the device housing 4 which is proximal to the discharge outlet of the aerosol generator. The housing is interconnected to the downwardly projecting outlet sleeve. This interconnectedness may be achieved by incorporating the housing and the sleeve into a single integral unit or by the two pieces being subsequently attached. It is preferable for the housing to have a removable top 6 that allows access to the aerosol generator located inside. The medicated particles remain in the containment region until, by the force of gravity, they begin to move downward into and through the outlet sleeve 8. The outlet sleeve show here is downwardly convergent. It is also possible to use an outlet sleeve that is substantially cylindrical. This would be the case when using a nebulizer with small diameter high density output. The sleeve channels the particles to the medication rich region 16 located proximal to the sleeve's lower opening, which is positioned above the patient's nose and mouth. The medicated particles may then be inhaled by the patient by way of tidal breathing. The air movement deflector 10, here shown as rigid, inhibits ambient air movement that may disperse the medication rich region. Since the device is suspended above the patient, and the air movement deflector does not create a sealed environment, the deflector may be constructed of any suitable material, be it rigid or flexible, clear, opaque, or with graphics that would be of interest to a particular patient group. The non-sealing deflector also allows for claming parental contact on areas such as the cheek or forehead. It should be noted that a rigid deflector might be used to suspend the other elements of the device above the nose and mouth of the patient.

Figure 2:
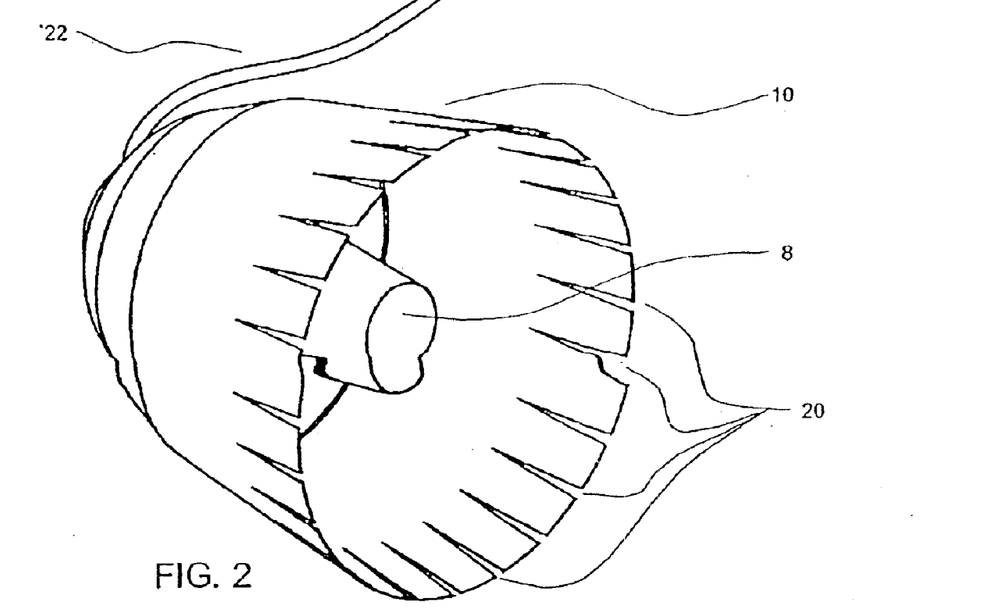
FIG. 2 is an isometric view of a preferred embodiment of the present invention, the view being from the bottom of the device.

FIG. 2 shows the underside of a preferred embodiment of the present invention that utilizes a flexible deflector 10, into which slits 20 are cut to accommodate changes in surface heights as the device encloses the patient's bead. Also shown are the outlet sleeve 8 and the air hose 22 for the nebulizer, which is used as the aerosol generator.

Figure 3:
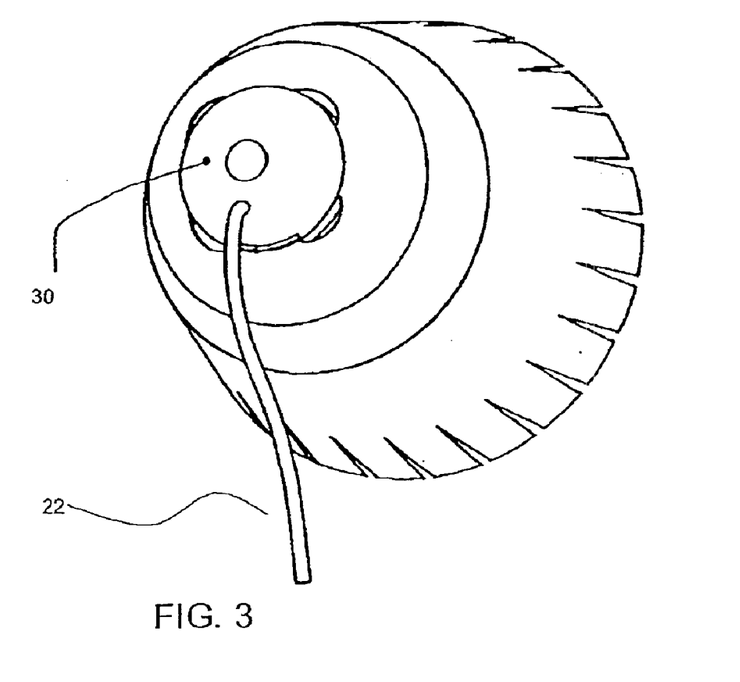
FIG. 3 is an isometric view of a preferred embodiment of the present invention, the view being from the top of the device.

FIG. 3 shows the same embodiment as FIG. 2, however, this view shows a preferably removable top 30 for the containment region housing. Removal of this top allows access to the aerosol generator that is located inside the housing. Also shown is the air hose 22 for the nebulizer, which is used as the aerosol generator.

Figure 4:
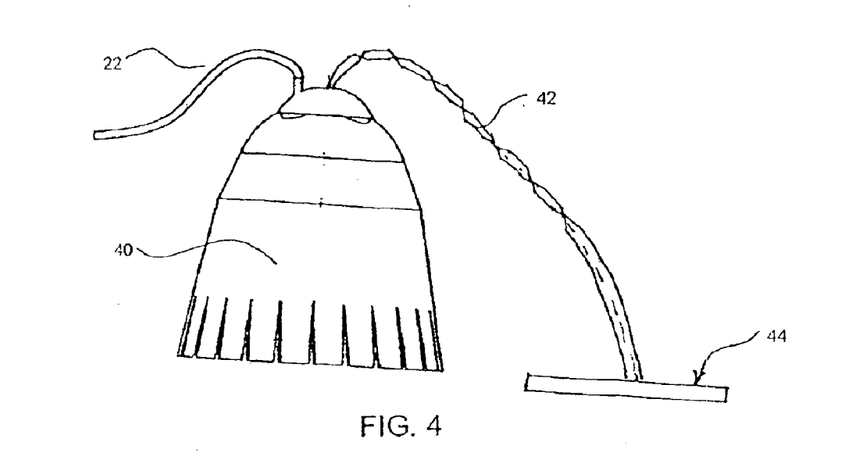
FIG. 4 is a schematic view of a preferred embodiment of the present invention suspended from a flexible stand.

In FIG. 4, a preferred embodiment of the present invention 40 is shown suspended from a flexible stand 42 that is attached to a base 44. Also shown is the air hose 22 for the nebulizer, which is used as the aerosol generator.

Figure 5:
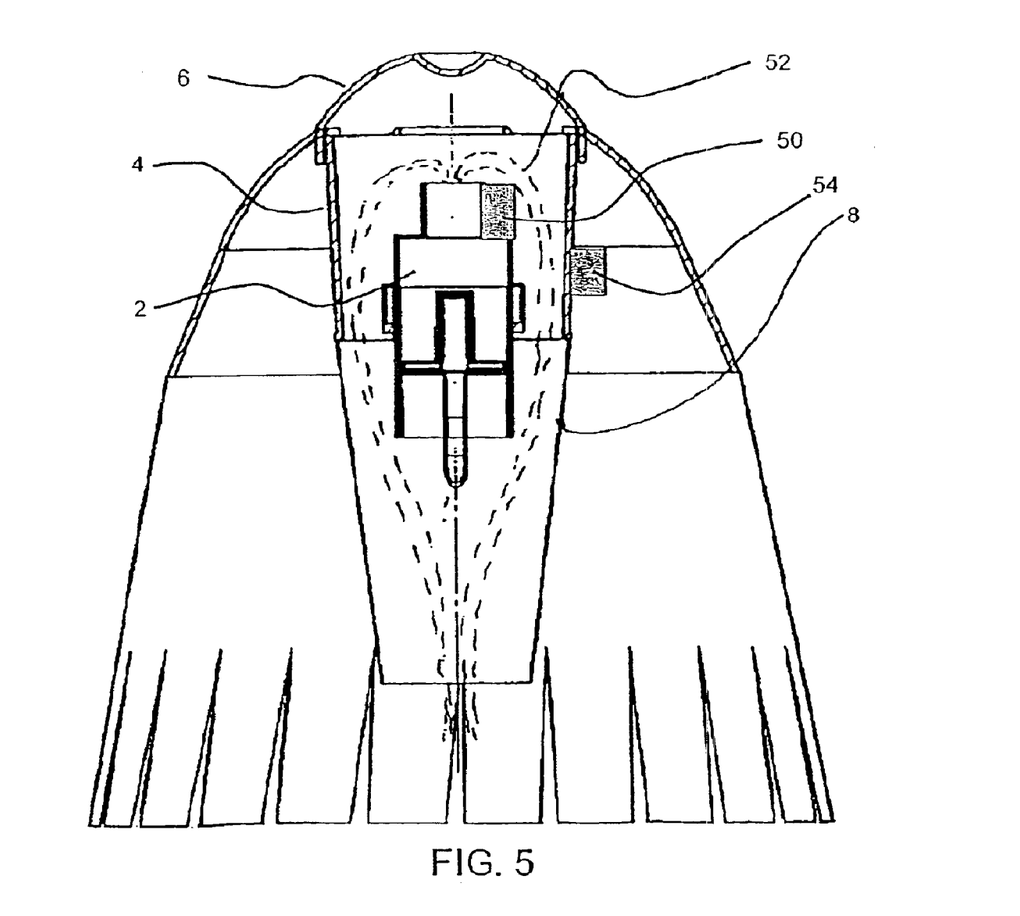
FIG. 5 is a cross-sectional schematic view of a preferred embodiment of the present invention in which the aerosol particles and the interior surfaces of the device are electrically charged with like charges.
Figure 6:
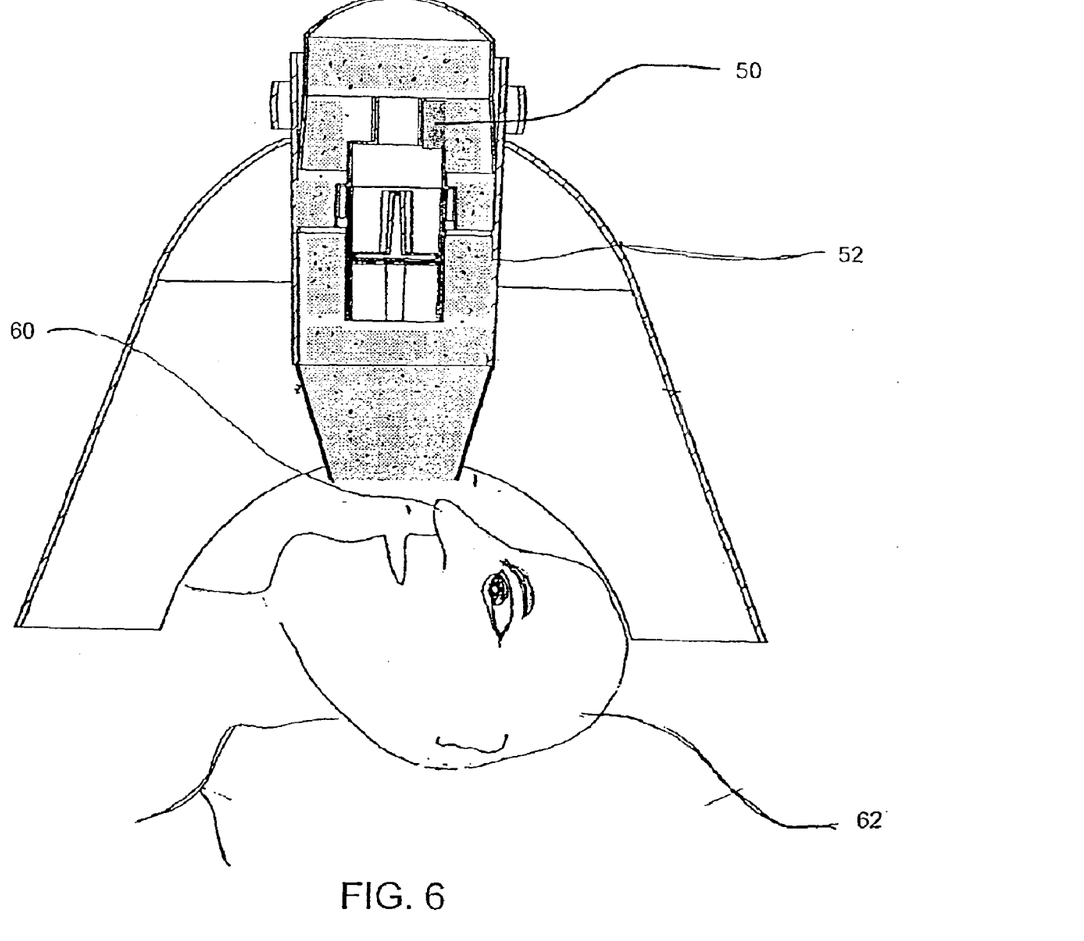
FIG. 6 is a cross-sectional schematic of a preferred embodiment of the present invention, in which the aerosol particles are electrically charged and the patient is electrically grounded.

FIG. 5 shows a second preferred embodiment of the present invention that electrically charges the aerosol particles 52, by use of an electrical charging device 50, which is part of an electrical charging system. The example shown here charges the particles as they leave the aerosol generator, however, the charging process may take place anywhere along the path of the particles between the point of aerosol generation and the point at which the particles leave the outlet sleeve. The sytem further charges the surfaces of the aerosol generator 2, housing 4 and top 6, and the outlet sleeve 8, or at least one separate electrode, with a like charge to the charge of the particles. In the example shown here, the surfaces are charged by use of a second electrical charging device 54. Since like charges repel, the particles are encouraged to start a downward flow more quickly and the downward flow of the particles is enhanced due to a lessened chance that the particles will settle on any of the device surfaces FIG. 6 shows a third preferred embodiment of the present invention that gives the aerosol particles an electrical charge by use of an electrical charging device 50, which is part of an electrical charging system. The patient 62 is electrically grounded and the downward flow of the charged particles 52 is enhanced as the particles are drawn, by electrostatic attraction, to the mouth and nose 60 of the patient.

Figure 7:
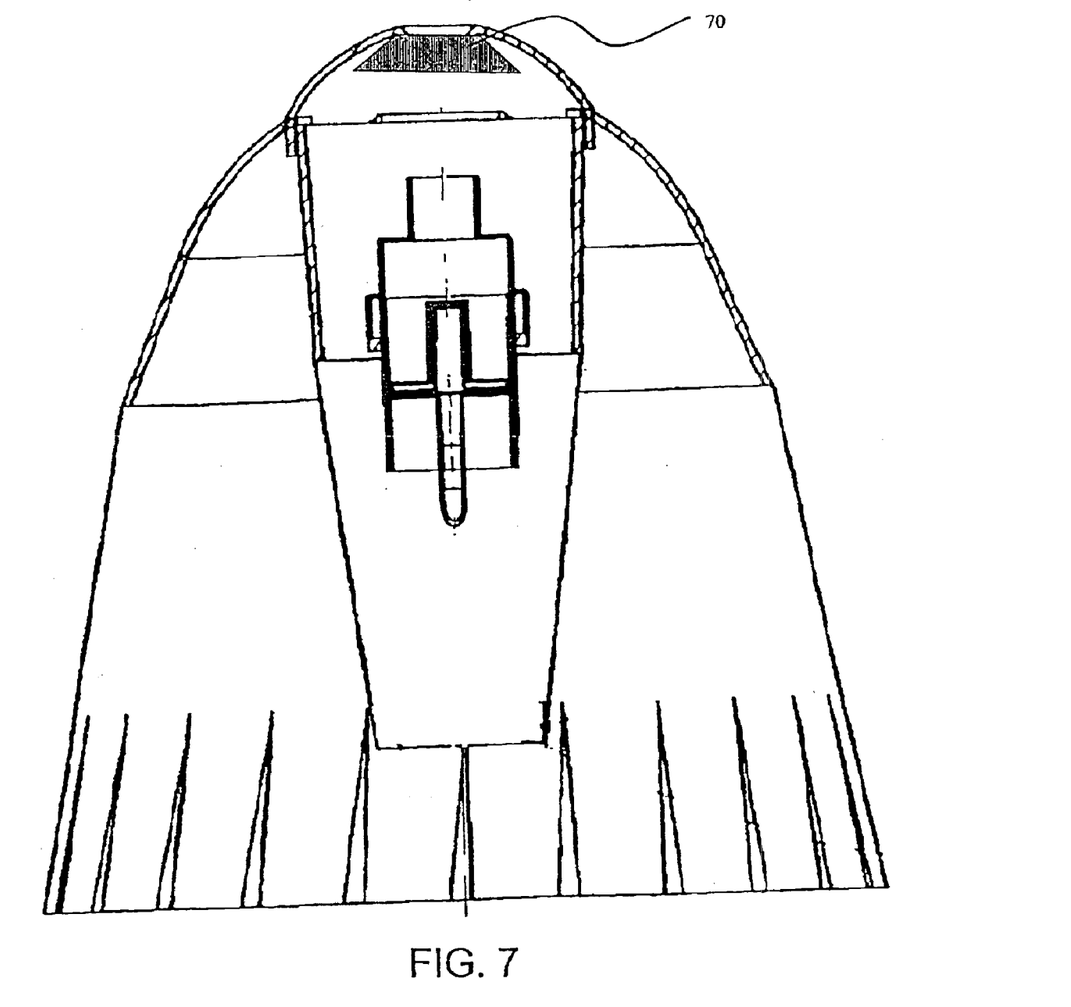
FIG. 7 is cross-sectional schematic of a preferred embodiment of the present invention, in which the downward flow of the aerosol particles is enhanced by downward air movement.
Figure 8:
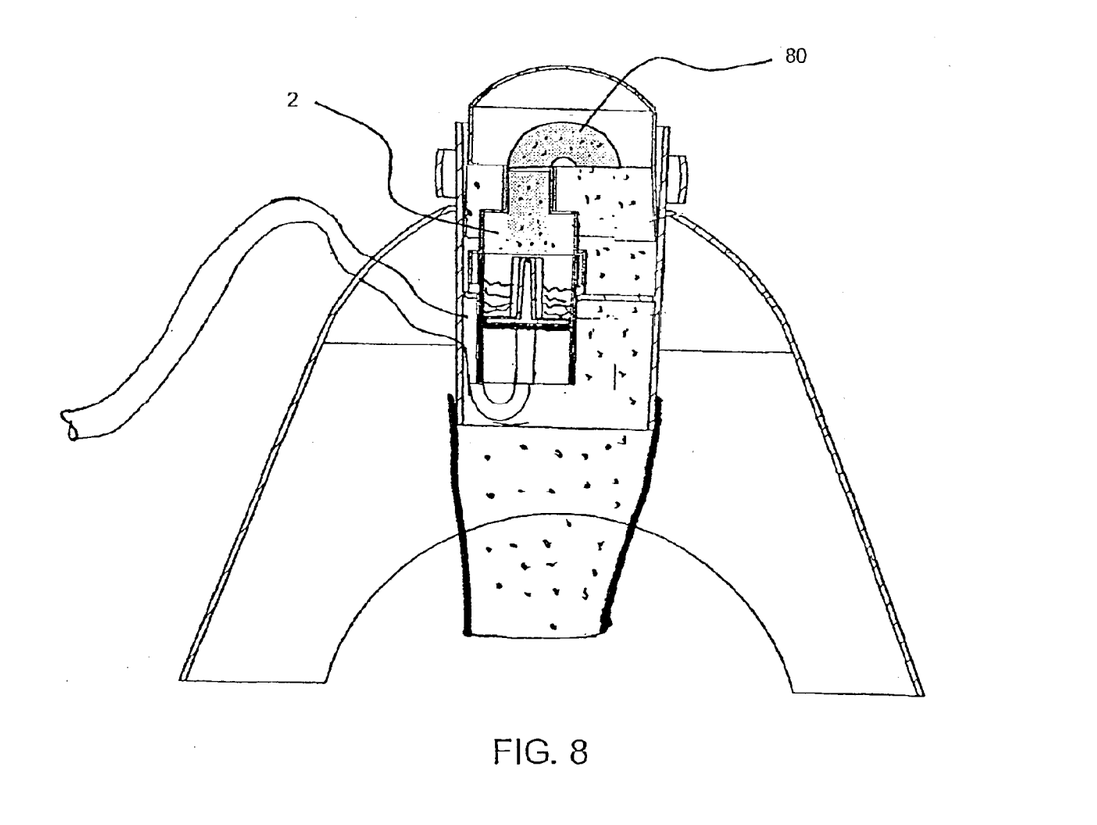
FIG. 8 is a cross-sectional schematic view of a preferred embodiment of the present invention, in which the aerosol is discharged in a downward direction.

FIG. 7 shows a fourth preferred embodiment of the present invention into which an airflow device 70, such as but not limited to, a fan, to enhance the downward flow of the aerosol particles from the containment region into and through the outlet sleeve. FIG. 8 shows a fifth preferred embodiment of the present invention that uses an aerosol generator that discharges the aerosol in a downward direction. Shown here is a nebulizer 2 equipped with a downwardly turned nozzle 80.

Figure 9:
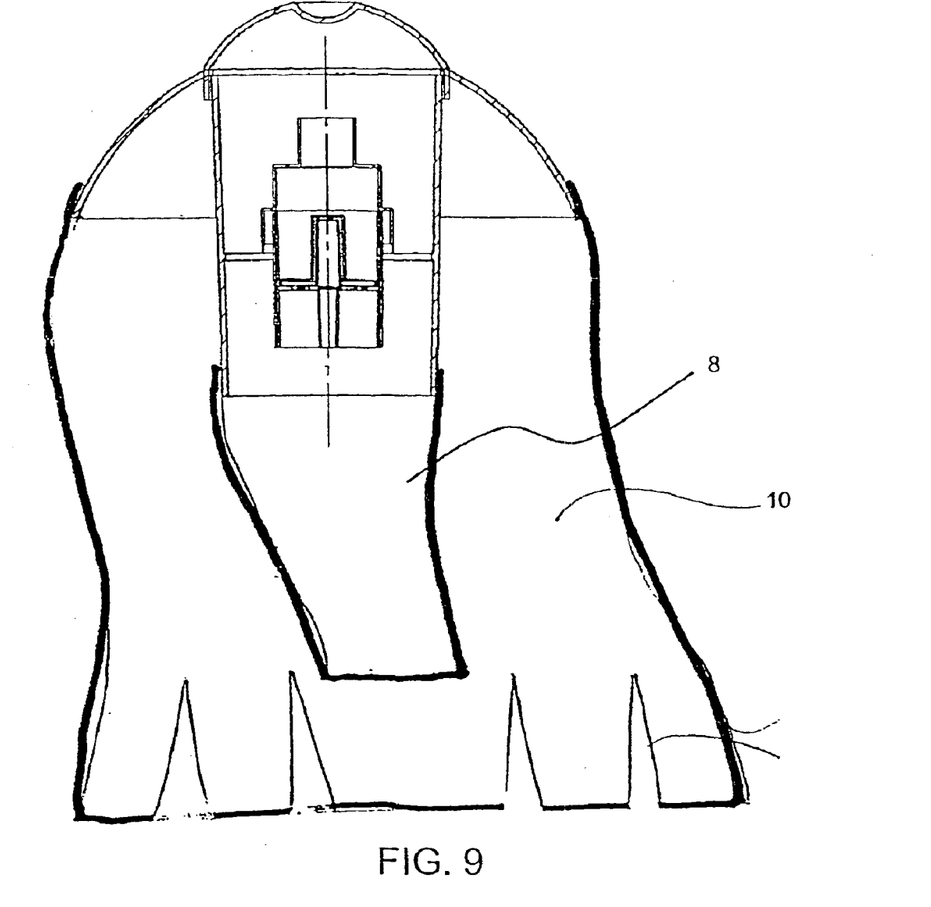
FIG. 9 is a cross-sectional schematic view of a preferred embodiment of the present invention, in which the outlet sleeve and the air movement deflector are constructed of flexible material.

FIG. 9 shows a highly flexible material for the outlet sleeve 8 and the air movement deflector 10, which may be used with any preferred embodiment of the present invention.

Figure 10:
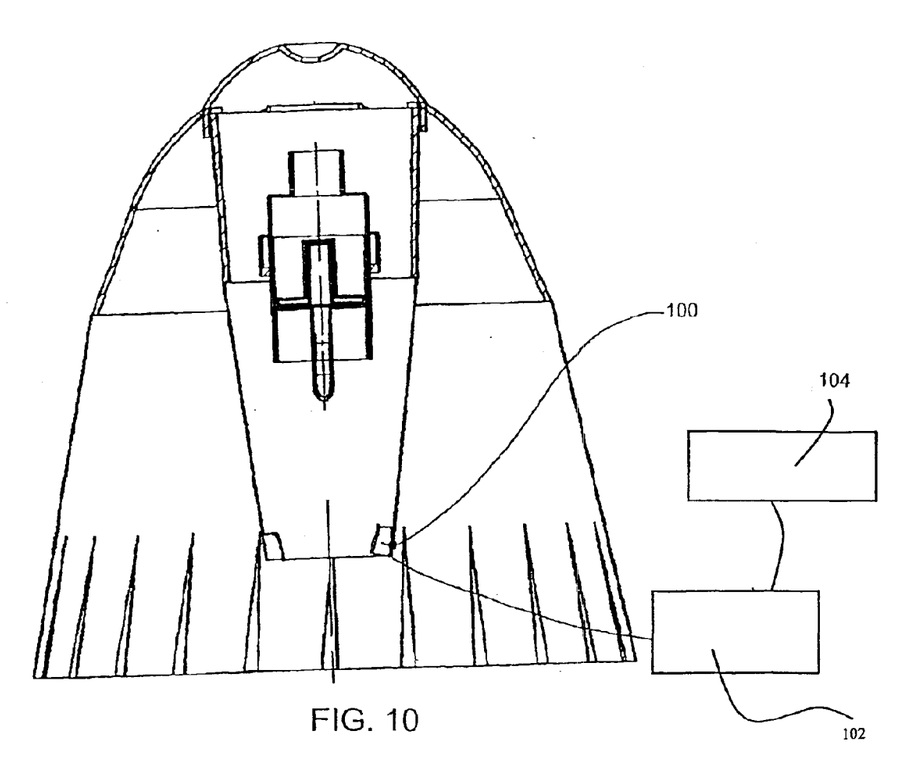
FIG. 10 is a cross-sectional schematic view of a preferred embodiment of the present invention, to which a tidal breathing monitor, data processing unit and a control unit have been appended.

FIG. 10 shows a preferred embodiment of the present invention onto which a sensing device 100 of a tidal breathing monitor has been appended. The sensing device is connected to a processing unit 102, which sends data to a control unit 104. Any of the embodiments of the present invention may be used in conjunction with a control system, which may further include a tidal breathing monitor, such as, but not limited to, devices that monitor breathing by way of audio, temperature, air flow, or physically, such as chest expansion.

The use of a tidal breathing monitor as part of a control system, in conjunction with an aerosol inhalation therapy device, produces a method for monitoring and determining the effectiveness of the aerosol inhalation therapy, while the therapy is in progress. This is done by using the tidal breathing monitor to establish a baseline tidal breathing rate. Therapy with an inhalation therapy device is begun, and tidal breathing is monitored throughout the therapy. This method of monitoring can supply the medical personnel, or parents, with data relating to the effectiveness of the treatment. Further, the control system may be programmed to regulate the operational elements of the device during therapy. As a non-limiting example, the tidal breathing of a patient before therapy begins may be rapid and shallow. As the therapy progresses the tidal breathing may begin to slow and become deeper. The control system would monitor the changes, and when the tidal breathing reaches a predetermined rate, the control system would discontinue therapy and alert the medical staff. The control system may also discontinue treatment when any other desired outcome has been reached. The control system and monitor also supply an important safety feature, in that the control system may discontinue therapy if the data shows there has been no further increase in treatment effectiveness, the treatment has reached the desired level of effectiveness or a predetermined amount of time has elapsed.

It will be appreciated that the above descriptions are intended only to serve as examples, and that many other embodiments are possible within the spirit and the scope of the present invention.

What is claimed is:

1. A device for delivering a flow of aerosol medication to a patient breathing tidally and positioned supinely, the device adapted to be suspended above the patient's nose and mouth, said device comprising:

(a) an aerosol generator, which generates a medicated aerosol;

(b) a housing associated with said aerosol generator, defining a containment region, into which said generator discharges said aerosol, said housing preventing the immediate dispersal of particles of said aerosol;

(c) a downwardly projecting outlet sleeve interconnected to a bottom of said housing, so that said particles move into and through said outlet sleeve, said outlet sleeve channeling said particles to a region externally proximal to a bottom opening of said outlet sleeve; and (d) an air movement deflector, configured to inhibit the dispersion of said particles once said particles arrive at said external region, by reducing ambient air movement.

2. The device of claim 1, wherein said outlet sleeve is downwardly convergent.

3. The device of claim 1, wherein said outlet sleeve is substantially cylindrical.

4. The device of claim 1, wherein said aerosol generator discharges said aerosol in an upward direction.

5. The device of claim 4, wherein said downward flow of said particles into and through said outlet sleeve is solely by gravitational force.

6. The device of claim 4, further comprising an electrical system, which includes at least one charging device, whereby said particles are electrically charged.

7. The device of claim 6, wherein said electrical charging system further charges surfaces of said housing that define said containment region and said outlet sleeve, said surfaces, said outlet sleeve and said particles being like charged so as to diminish a possible settling of said particles on said surfaces and said outlet sleeve due to electrostatic repulsion.

8. The device of claim 6, wherein said electrical charging system further includes a charged electrode, said electrode and said particles being like charged so as to enhance said downward flow due to electrostatic repulsion.

9. The device of claim 6, further comprising an electrical grounding device by which said patient is electrically grounded so as to facilitate said downward flow by way of electrostatic attraction.

10. The device of claim 4, further comprising an airflow generator that moves air downwardly from said containment region, enhancing said downward flow of particles.

11. The device of claim 1, wherein said aerosol generator discharges said aerosol in a downward direction.

12. The device of claim 1, wherein said deflector is non-sealing allowing for exchange of air.

13. The device of claim 1, further comprising a control system which regulates the operational elements of said device, including a tidal breathing monitor deployed to monitor the tidal breathing of said patient.

14. A method for delivery of a flow of aerosol medication to a patient breathing tidally and positioned supinely, by a device adapted to be suspended above said patient's nose and mouth, said method comprising:

(a) generating an aerosol of medicated particles;

(b) discharging said aerosol in a containment region, said region being defined by a housing, said housing preventing the immediate dispersal of said particles;

(c) channeling said particles, by use of a downwardly projecting outlet sleeve, toward a region externally proximal to a bottom opening of said outlet sleeve, so as to create a medication rich environment in said external region; and (d) deploying an element configured so as to inhibit the dispersion of said particles once said particles arrive at said external region, by reducing ambient air movement.

15. The method of claim 14, wherein said discharging is in an upward direction.

16. The method of claim 15, wherein said particles begin to flow downward into and through said outlet sleeve, solely by gravitational force.

17. The method of claim 15, further comprising charging said particles.

18. The method of claim 17, further comprising charging the surfaces of said housing and said outlet sleeve, said surfaces and said particles being like charged, so as to diminish a possible settling of said particles on said surfaces, due to electrostatic repulsion.

19. The method of claim 17, further comprising charging of at least one electrode, said electrode and said particles being like charged, so as to enhance said downward flow, due to electrostatic repulsion.

20. The method of claim 17, further comprising electrically grounding said patient, by use of an electrical grounding device, so as to enhance said downward flow by way of electrostatic attraction.

21. The method of claim 15, further comprising enhancing said downward flow by use of downwardly flowing air movement.

22. The method of claim 14, wherein said discharge is in a downward direction.

23. The method of claim 14, further comprising regulating the operational elements of said device by a control system, which is further connected to a tidal breathing monitor.

* * * * *